(12) United States Patent
Yang et al.

(10) Patent No.: US 11,254,730 B2
(45) Date of Patent: Feb. 22, 2022

(54) N-TERMINAL RECOMBINANT PROTEIN OF CCR4 AND USE THEREOF

(71) Applicant: INSTITUTE OF BIOPHYSICS, CHINESE ACADEMY OF SCIENCES, Beijing (CN)

(72) Inventors: Pengyuan Yang, Beijing (CN); Yanan Gao, Beijing (CN); Maojun You, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/758,825

(22) PCT Filed: Nov. 14, 2018

(86) PCT No.: PCT/CN2018/115442
§ 371 (c)(1),
(2) Date: Apr. 23, 2020

(87) PCT Pub. No.: WO2019/161684
PCT Pub. Date: Aug. 29, 2019

(65) Prior Publication Data
US 2020/0339660 A1    Oct. 29, 2020

(30) Foreign Application Priority Data
Feb. 23, 2018  (CN) .......................... 201810154860.9

(51) Int. Cl.
| | | |
|---|---|---|
| A61K 38/17 | (2006.01) | |
| A61K 47/68 | (2017.01) | |
| C07K 14/715 | (2006.01) | |
| C07K 19/00 | (2006.01) | |
| A61K 38/00 | (2006.01) | |

(52) U.S. Cl.
CPC ...... *C07K 14/7158* (2013.01); *A61K 38/1793* (2013.01); *A61K 47/6811* (2017.08); *A61K 38/00* (2013.01); *C07K 2319/30* (2013.01)

(58) Field of Classification Search
CPC .............. A61K 38/177; A61K 38/1793; A61K 47/6811; C07K 14/705; C07K 14/70596; C07K 14/7158; C07K 2319/30
See application file for complete search history.

(56) References Cited

U.S. PATENT DOCUMENTS

| | | | |
|---|---|---|---|
| 7,504,104 B2* | 3/2009 | Shitara ..................... | A61P 37/00 424/139.1 |
| 8,895,007 B2* | 11/2014 | Hagemann .............. | A61P 35/00 424/143.1 |
| 2011/0178021 A1* | 7/2011 | Rougeot ............ | A61K 38/1709 514/17.6 |
| 2012/0020962 A1 | 1/2012 | Ueda et al. | |
| 2015/0354001 A1* | 12/2015 | Porath .............. | G01N 33/48721 204/543 |
| 2016/0347827 A1* | 12/2016 | Yee-Peng ........... | C07K 16/1027 |
| 2017/0267730 A1* | 9/2017 | McPhee ................. | A61K 9/107 |
| 2020/0129581 A1* | 4/2020 | Kim ........................ | A61K 38/16 |

FOREIGN PATENT DOCUMENTS

| | | |
|---|---|---|
| CN | 106421796 A | 2/2017 |
| GN | 105722531 A | 6/2016 |
| JP | 4052515 B2 | 2/2008 |
| JP | 2012020962 A | 2/2012 |
| JP | 2014513519 A | 6/2014 |
| JP | 2015517470 A | 6/2015 |
| WO | WO 2005/049799 A2 | 6/2005 |
| WO | WO 2008/143910 A2 | 11/2008 |
| WO | WO 2011/030841 A1 | 3/2011 |

OTHER PUBLICATIONS

International Search Report, PCT/CN2018/115442, dated Feb. 13, 2019.
Written Opinions in Chinese, PCT/CN2018/115442, dated Feb. 13, 2019.
Chinese First Office Action, in corresponding Chinese Application No. CN2018101548609, dated Feb. 27, 2020.
Sun, Zhe, et al. "Interactions of Peptides from Secreted Human CKLF1 and the N-Terminal Extracellular Tail of CCR4 Analyzed by CZE," Chromatographia (2009), 70, July (No. 1/2): 287-292.
Supplemental European Search Report, EP Patent Application No. 18 90 7350.5, dated Jan. 11, 2021.
Abboud, Dayana, et al., "A strategy to discovery decoy chemokine ligands with an anti-inflammatory activity," Scientific Reports, vol. 5, Oct. 7, 2015, pp. 1-14.
Hutchings, Catherine J., et al., "Opportunities for therapeutic antibodies directed at G-protein-coupled receptors," Nature Review, vol. 16, No. 11, Jul. 14, 2017, pp. 787-810.
DATABASE UniProt [Online] Oct. 1, 1996 "ID CCR4_HUMAN", XP002801291, retrieved from EBI Accession No. P51679.
Japanese Office Action in Japanese Application No. 2020-534529 dated Aug. 3, 2021.
Sun, Zhe, et al., "Interactions of Peptides from Secreted Human CKLF1 and the N-Terminal Extracellular Tail of CCR4 Analyzed by CZE", Chromatographia (2009), vol. 70, No. 1-2, pp. 287-292.

* cited by examiner

*Primary Examiner* — Jeffrey E. Russel
(74) *Attorney, Agent, or Firm* — Knobbe, Martens, Olson & Bear, LLP (57) ABSTRACT

The present invention provides a recombinant protein or a derivative thereof, wherein the recombinant protein has an amino acid sequence of the N-terminal portion of CC chemokine receptor 4 (CCR4). The invention also provides the use of the recombinant protein or a derivative thereof for treating or preventing a disease or condition associated with CCR4 signaling, such as an allergic disease, inflammatory enteritis, psoriasis, an inflammatory skin disease, vasculitis, spondyloarthropathy, scleroderma, asthma, a respiratory allergic disease, an autoimmune disease, graft rejection, leukemia, lymphoma, a blood-borne cancer, a disease requiring inhibition of undesirable inflammation, and a cancer.

18 Claims, 5 Drawing Sheets
Specification includes a Sequence Listing.

Fig.1A prediction of Gibbs free energy ΔG

SEQUENCE LISTING

```
<160> NUMBER OF SEQ ID NOS: 14

<210> SEQ ID NO 1
<211> LENGTH: 47
<212> TYPE: PRT
<213> ORGANISM: Artificial
<220> FEATURE:
<223> OTHER INFORMATION: N-CCR4 protein

<400> SEQUENCE: 1

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Leu Tyr Ser
        35                  40                  45

<210> SEQ ID NO 2
<211> LENGTH: 183
<212> TYPE: PRT
<213> ORGANISM: Artificial
<220> FEATURE:
<223> OTHER INFORMATION: (N-CCR4)3 protein

<400> SEQUENCE: 2

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
            20                  25                  30

Gly Ile Lys Ala Phe Gly Glu Leu Phe Leu Pro Leu Tyr Ser Gly
        35                  40                  45

Gly Gly Gly Ser Gly Gly Gly Gly Ser Met Asn Pro Thr Asp Ile Ala
    50                  55                  60
```

-continued

```
Asp Thr Thr Leu Asp Glu Ser Ile Tyr Ser Asn Tyr Tyr Leu Tyr Glu
 65                  70                  75                  80

Ser Ile Pro Lys Pro Cys Thr Lys Glu Gly Ile Lys Ala Phe Gly Glu
                 85                  90                  95

Leu Phe Leu Pro Pro Leu Tyr Ser Gly Gly Gly Gly Ser Gly Gly Gly
                100                 105                 110

Gly Ser Met Asn Pro Thr Asp Ile Ala Asp Thr Thr Leu Asp Glu Ser
            115                 120                 125

Ile Tyr Ser Asn Tyr Tyr Leu Tyr Glu Ser Ile Pro Lys Pro Cys Thr
        130                 135                 140

Lys Glu Gly Ile Lys Ala Phe Gly Glu Leu Phe Leu Pro Pro Leu Tyr
145                 150                 155                 160

Ser Leu Asp Pro Asn Ser Ser Val Asp Lys Leu Ala Ala Ala Leu
                165                 170                 175

Glu His His His His His His
            180
```

```
<210> SEQ ID NO 3
<211> LENGTH: 390
<212> TYPE: PRT
<213> ORGANISM: Artificial
<220> FEATURE:
<223> OTHER INFORMATION: (N-CCR4)3-Fc protein

<400> SEQUENCE: 3

Met Asn Pro Thr Asp Ile Ala Asp Thr Thr Leu Asp Glu Ser Ile Tyr
 1               5                  10                  15

Ser Asn Tyr Tyr Leu Tyr Glu Ser Ile Pro Lys Pro Cys Thr Lys Glu
             20                  25                  30

Gly Ile Lys Ala Phe Gly Glu Leu Phe Leu Pro Pro Leu Tyr Ser Gly
         35                  40                  45

Gly Gly Ser Gly Gly Gly Gly Ser Met Asn Pro Thr Asp Ile Ala
     50                  55                  60

Asp Thr Thr Leu Asp Glu Ser Ile Tyr Ser Asn Tyr Tyr Leu Tyr Glu
 65                  70                  75                  80

Ser Ile Pro Lys Pro Cys Thr Lys Glu Gly Ile Lys Ala Phe Gly Glu
                 85                  90                  95

Leu Phe Leu Pro Pro Leu Tyr Ser Gly Gly Gly Gly Ser Gly Gly Gly
                100                 105                 110

Gly Ser Met Asn Pro Thr Asp Ile Ala Asp Thr Thr Leu Asp Glu Ser
            115                 120                 125

Ile Tyr Ser Asn Tyr Tyr Leu Tyr Glu Ser Ile Pro Lys Pro Cys Thr
        130                 135                 140

Lys Glu Gly Ile Lys Ala Phe Gly Glu Leu Phe Leu Pro Pro Leu Tyr
145                 150                 155                 160

Ser Lys Leu Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
                180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
        210                 215                 220

Val Glu Val His Asn Ala Lys Thr Lys Pro Arg Glu Glu Gln Tyr Asn
225                 230                 235                 240
```

```
Ser Thr Tyr Arg Val Val Ser Val Leu Thr Val Leu His Gln Asp Trp
            245                 250                 255

Leu Asn Gly Lys Glu Tyr Lys Cys Lys Val Ser Asn Lys Ala Leu Pro
        260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
        290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
            325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
            355                 360                 365

Ser Val Met His Glu Gly Leu His Asn His Tyr Thr Gln Lys Ser Leu
        370                 375                 380

Ser Leu Ser Pro Gly Lys
385                 390

<210> SEQ ID NO 4
<211> LENGTH: 549
<212> TYPE: DNA
<213> ORGANISM: Artificial
<220> FEATURE:
<223> OTHER INFORMATION: codon optimized sequence of (N-CCR4)3 protein
      DNA

<400> SEQUENCE: 4
atgaatccga ccgatattgc agataccaca ctggatgaaa gcatctatag caactattat      60
ctgtatgaga gcattccgaa accgtgtacc aaagaaggta ttaaagcatt tggcgaactg     120
tttctgcctc cgctgtatag cggtggtggt ggtagtggtg gcggtggttc aatgaacccg     180
acagatatcg ccgacacaac cctggatgaa tcaatttatt ccaactacta cctgtacgag     240
tcaatcccga aaccttgcac aaaagagggc atcaaagcct tggtgagctg ttttttaccg     300
cctctgtatt caggcggtgg cggtagcgga ggtggcggaa gcatgaatcc tacagacatt     360
gcggatacga ccctggacga gagcatttat tcaaattact attatacga aagcatcccg      420 aagccatgta cgaaagaggg aattaaggcg ttcggtgaat tatttctgcc accgttatat     480
agcttggatc cgaattcgag ctccgtcgac aagcttgcgg ccgcactcga gcaccaccac     540
caccaccac                                                            549

<210> SEQ ID NO 5
<211> LENGTH: 1242
<212> TYPE: DNA
<213> ORGANISM: Artificial
<220> FEATURE:
<223> OTHER INFORMATION: (N-CCR4)3-Fc DNA

<400> SEQUENCE: 5
atggagacag acacactcct gctatgggta ctgctgctct gggttccagg ttccactggt      60
gactcgatga accccaccga catcgccgac accaccctcg acgagagcat ctacagcaac     120
tactacctgt acgaaagcat ccccaaaccc tgcaccaaag aaggcatcaa agccttcggc     180
gagctgttcc tcccccccct gtacagcggc ggcggtggat ctggcggcgg aggatcaatg     240
```

| | |
|---|---|
| aaccccacag acatcgccga taccaccctg gacgaaagca tttacagcaa ttactacctg | 300 |
| tatgagtcca tccccaaacc ttgcaccaaa gagggcatca aggccttcgg cgaactgttc | 360 |
| ctcccacccc tgtacagtgg cggcggcgga agcggaggcg gaggaagcat gaaccccact | 420 |
| gacatcgccg acacaaccct cgacgaaagc atatacagca attattacct gtacgagtcc | 480 |
| atccctaaac cctgcacaaa ggaaggcatc aaggcattcg gagagctgtt cctgcccccc | 540 |
| ctgtatagca agcttgacaa aactcacaca tgcccaccgt gcccagcacc tgaactcctg | 600 |
| gggggaccgt cagtcttcct cttccccccca aacccaagg acaccctcat gatctcccgg | 660 |
| acccctgagg tcacatgcgt ggtggtggac gtgagccacg aagaccctga ggtcaagttc | 720 |
| aactggtacg tggacggcgt ggaggtgcat aatgccaaga caaagccgcg ggaggagcag | 780 |
| tacaacagca cgtaccgtgt ggtcagcgtc ctcaccgtcc tgcaccagga ctggctgaat | 840 |
| ggcaaggagt acaagtgcaa ggtctccaac aaagcccctcc cagcccccat cgagaaaacc | 900 |
| atctccaaag ccaaagggca gccccgagaa ccacaggtgt acaccctgcc cccatcccgg | 960 |
| gatgagctga ccaagaacca ggtcagcctg acctgcctgg tcaaaggctt ctatcccagc | 1020 |
| gacatcgccg tggagtggga gagcaatggg cagccggaga caactacaa gaccacgcct | 1080 |
| cccgtgctga ctccgacgg ctccttcttc ctctacagca agctcaccgt ggacaagagc | 1140 |
| aggtggcagc aggggaacgt cttctcatgc tccgtgatgc atgagggtct gcacaaccac | 1200 |
| tacacgcaga agagcctctc cctgtctccg ggtaaataat aa | 1242 |

<210> SEQ ID NO 6
<211> LENGTH: 885
<212> TYPE: DNA
<213> ORGANISM: Artificial
<220> FEATURE:
<223> OTHER INFORMATION: CCL22-GST DNA

<400> SEQUENCE: 6

| | |
|---|---|
| atgggtccgt atggtgcaaa tatggaagat agcgtttgtt gccgtgatta tgttcgttat | 60 |
| cgtctgccgc tgcgtgttgt taaacacttt tattggacca gcgatagctg tccgcgtccg | 120 |
| ggtgttgttc tgctgaccct tcgtgataaa gaaatttgtg cagatccgcg tgttccgtgg | 180 |
| gttaaaatga ttctgaataa actgagccag gatccgggtg gcccgggtat gtcccctata | 240 |
| ctaggttatt ggaaaattaa gggccttgtg caacccactc gacttctttt ggaatatctt | 300 |
| gaagaaaaat atgaagagca tttgtatgag cgcgatgaag gtgataaatg cgaaacaaa | 360 |
| aagtttgaat gggtttggga gtttcccaat cttccttatt atattgatgg tgatgttaaa | 420 |
| ttaacacagt ctatggccat catacgttat atagctgaca agcacaacat gttgggtggt | 480 |
| tgtccaaaag agcgtgcaga gatttcaatg cttgaaggag cggttttgga tattagatac | 540 |
| ggtgtttcga gaattgcata tagtaaagac tttgaaactc tcaaagttga ttttcttagc | 600 |
| aagctacctg aaatgctgaa aatgttcgaa gatcgtttat gtcataaaac atatttaaat | 660 |
| ggtgatcatg taacccatcc tgacttcatg ttgtatgacg ctcttgatgt tgttttatac | 720 |
| atggacccaa tgtgcctgga tgcgttccca aaattagttt gttttaaaaa acgtattgaa | 780 |
| gctatcccac aaattgataa gtacttgaaa tccagcaagt atatagcatg gcctttgcag | 840 |
| ggctggcaag ccacgtttgg tggtggcgac catcctccaa aatga | 885 |

<210> SEQ ID NO 7
<211> LENGTH: 294
<212> TYPE: PRT
<213> ORGANISM: Artificial

```
<220> FEATURE:
<223> OTHER INFORMATION: CCL22-GST protein

<400> SEQUENCE: 7

Met Gly Pro Tyr Gly Ala Asn Met Glu Asp Ser Val Cys Cys Arg Asp
1               5                   10                  15

Tyr Val Arg Tyr Arg Leu Pro Leu Arg Val Val Lys His Phe Tyr Trp
            20                  25                  30

Thr Ser Asp Ser Cys Pro Arg Pro Gly Val Val Leu Leu Thr Phe Arg
        35                  40                  45

Asp Lys Glu Ile Cys Ala Asp Pro Arg Val Pro Trp Val Lys Met Ile
    50                  55                  60

Leu Asn Lys Leu Ser Gln Asp Pro Gly Pro Gly Met Ser Pro Ile
65                  70                  75                  80

Leu Gly Tyr Trp Lys Ile Lys Gly Leu Val Gln Pro Thr Arg Leu Leu
            85                  90                  95

Leu Glu Tyr Leu Glu Glu Lys Tyr Glu Glu His Leu Tyr Glu Arg Asp
            100                 105                 110

Glu Gly Asp Lys Trp Arg Asn Lys Lys Phe Glu Leu Gly Leu Glu Phe
        115                 120                 125

Pro Asn Leu Pro Tyr Tyr Ile Asp Gly Asp Val Lys Leu Thr Gln Ser
    130                 135                 140

Met Ala Ile Ile Arg Tyr Ile Ala Asp Lys His Asn Met Leu Gly Gly
145                 150                 155                 160

Cys Pro Lys Glu Arg Ala Glu Ile Ser Met Leu Glu Gly Ala Val Leu
            165                 170                 175

Asp Ile Arg Tyr Gly Val Ser Arg Ile Ala Tyr Ser Lys Asp Phe Glu
            180                 185                 190

Thr Leu Lys Val Asp Phe Leu Ser Lys Leu Pro Glu Met Leu Lys Met
        195                 200                 205

Phe Glu Asp Arg Leu Cys His Lys Thr Tyr Leu Asn Gly Asp His Val
    210                 215                 220

Thr His Pro Asp Phe Met Leu Tyr Asp Ala Leu Asp Val Val Leu Tyr
225                 230                 235                 240

Met Asp Pro Met Cys Leu Asp Ala Phe Pro Lys Leu Val Cys Phe Lys
            245                 250                 255

Lys Arg Ile Glu Ala Ile Pro Gln Ile Asp Lys Tyr Leu Lys Ser Ser
            260                 265                 270

Lys Tyr Ile Ala Trp Pro Leu Gln Gly Trp Gln Ala Thr Phe Gly Gly
        275                 280                 285

Gly Asp His Pro Pro Lys
        290

<210> SEQ ID NO 8
<211> LENGTH: 23
<212> TYPE: PRT
<213> ORGANISM: Artificial Sequence
<220> FEATURE:
<223> OTHER INFORMATION: peptide sequence

<400> SEQUENCE: 8

Thr Ile Tyr Ser Ile Ile Phe Leu Thr Gly Ile Val Gly Asn Gly Leu
1               5                   10                  15

Val Ile Leu Val Met Gly Tyr
            20
```

-continued

```
<210> SEQ ID NO 9
<211> LENGTH: 23
<212> TYPE: PRT
<213> ORGANISM: Artificial Sequence
<220> FEATURE:
<223> OTHER INFORMATION: peptide sequence

<400> SEQUENCE: 9

Tyr Arg Leu His Leu Ser Val Ala Asp Leu Leu Phe Val Ile Thr Leu
1               5                   10                  15

Pro Phe Trp Ala Val Asp Ala
            20

<210> SEQ ID NO 10
<211> LENGTH: 23
<212> TYPE: PRT
<213> ORGANISM: Artificial Sequence
<220> FEATURE:
<223> OTHER INFORMATION: peptide sequence

<400> SEQUENCE: 10

Val Ile Tyr Thr Val Asn Leu Tyr Ser Ser Val Leu Ile Leu Ala Phe
1               5                   10                  15

Ile Ser Leu Asp Arg Tyr Leu
            20

<210> SEQ ID NO 11
<211> LENGTH: 21
<212> TYPE: PRT
<213> ORGANISM: Artificial Sequence
<220> FEATURE:
<223> OTHER INFORMATION: peptide sequence

<400> SEQUENCE: 11

Val Val Tyr Val Gly Val Trp Ile Pro Ala Leu Leu Leu Thr Ile Pro
1               5                   10                  15

Asp Phe Ile Phe Ala
            20

<210> SEQ ID NO 12
<211> LENGTH: 23
<212> TYPE: PRT
<213> ORGANISM: Artificial Sequence
<220> FEATURE:
<223> OTHER INFORMATION: peptide sequence

<400> SEQUENCE: 12

Ile Met Val Gly Leu Ile Leu Pro Gly Ile Val Ile Leu Ser Cys Tyr
1               5                   10                  15

Cys Ile Ile Ile Ser Lys Leu
            20

<210> SEQ ID NO 13
<211> LENGTH: 21
<212> TYPE: PRT
<213> ORGANISM: Artificial Sequence
<220> FEATURE:
<223> OTHER INFORMATION: peptide sequence

<400> SEQUENCE: 13

Ala Leu Lys Thr Thr Val Ile Leu Ile Leu Ala Phe Phe Ala Cys Trp
1               5                   10                  15

Leu Pro Tyr Tyr Ile
            20
```

```
<210> SEQ ID NO 14
<211> LENGTH: 23
<212> TYPE: PRT
<213> ORGANISM: Artificial sequence
<220> FEATURE:
<223> OTHER INFORMATION: peptide sequence

<400> SEQUENCE: 14

Trp Ile Ser Ile Thr Glu Ala Leu Ala Phe Phe His Cys Cys Leu Asn
1               5                   10                  15

Pro Ile Leu Tyr Ala Phe Leu
            20
```

N-TERMINAL RECOMBINANT PROTEIN OF CCR4 AND USE THEREOF

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 32600324_1.txt, the date of creation of the ASCII text file is Apr. 23, 2020, and the size of the ASCII text file is 14.2 KB.

TECHNICAL FIELD

The present invention relates to the technical field of biomedicine, and in particular to the application of N-terminal recombinant protein of CCR4, derivative compounds thereof, recombinant protein antibodies and other derivatives or compositions alone or in combination with other compounds or compositions having related uses, for treating, preventing, inhibiting or ameliorating cancers and diseases or conditions associated with CCR4 signaling.

BACKGROUND

The CC chemokine receptor 4 (CCR4), also known as CKR4, CMKBR4, ChemR13, K5-5 and the like, belongs to a CC chemokine receptor family, containing 360 amino acid residues, being located in p24-p21.3 region of chromosome 3, as a 7-transmembrane G protein-coupled receptor (GPCR), and is mainly expressed in various lymphocytes and tissues; and the high level expression of CCR4 is associated with a variety of inflammatory diseases, autoimmune diseases, hematological tumors, and the infiltration, metastasis and prognosis of malignant solid tumors. There are two known high-affinity ligands for CCR4: thymus and activation regulated chemokine (TARC/CCL 17) and the macrophage-derived chemokine (MDC/CCL 22). CCR4 chemoattracts different types of T cells to exert immune effects mainly by the binding of CCR4 expressed on the surface of Th2 cells, Th17 cells and regulatory T cells (Tregs) to its ligand CCL22/CCL17, for example Th2 cell plays an important pro-inflammatory role in asthma, respiratory allergic diseases and the like; Th17 cell induces inflammatory enteritis such as Crohn's disease, ulcerative colitis and autoimmune disease; CCR4 on the surface of Treg cells chemoattracts Treg cells by binding to its ligand CCL22/CCL17, causing immune escape, leading to adverse clinical consequences. Therefore, compounds that target CCR4 are expected to become a new strategy for the treatment of related diseases.

There are no reports on the crystal structure of CCR4 and CCL22, and the molecular mechanism of interaction between CCR4 and its ligand is unknown. At present, the two-step model is a widely accepted mechanism by which GPCRs bind to and activate it ligand. It believes that the N-terminus of GPCRs plays a very important role in the recognition of ligands. Therefore, by clearly knowing the N-terminal protein sequence of CCR4 and resolving the N-terminal protein structure of CCR4, CCR4 N-terminal recombinant protein can be effectively synthesized. By studying the function of the recombinant protein and developing its derivative compounds or antibodies, it is expected to competitively inhibit the CCL22/CCL17-CCR4 signaling pathway by targeting CCR4, alone or in combination with other compounds or compositions with related uses, for treating, preventing, inhibiting or ameliorating cancer and diseases or conditions related to CCR4 signaling, such as inflammatory diseases including allergic diseases, inflammatory enteritis, inflammatory skin diseases, asthma, autoimmune diseases and the like, graft rejection, hematological tumor such as leukemia, lymphoma and other blood-borne cancers such as cutaneous T cell lymphoma, acute lymphocytic leukemia and the like, and cancers including solid tumors and metastatic diseases such as gastric cancer, liver cancer, renal cancer, intestinal cancer, pancreatic cancer, lung cancer, bladder cancer, breast cancer, ovarian cancer, cervical cancer, melanoma, thyroid cancer, prostate cancer, nervous system tumor and the like. It has become a new strategy for immune-targeted therapy of related diseases, and has good clinical application prospects.

The currently commercially available CCR4 monoclonal antibody for treating tumors is mogamulizumab, which has a good therapeutic effect in the treatment or research of diseases such as cutaneous T cell lymphoma (CTCL), mycosis fungoides, Sézary syndrome, non-Hodgkin lymphoma and the like. The CCR4 receptor antagonist has a good therapeutic effect in the research of diseases such as asthma, rhinitis, dermatitis, thrombotic diseases, autoimmune diseases and the like.

However, to date, there has been no report on the use of N-terminal recombinant protein of CCR4 and derivative compounds thereof, recombinant protein antibodies and other derivatives or compositions alone or in combination with other compounds or compositions having related uses, for treating, preventing, inhibiting or ameliorating cancers and diseases or conditions associated with CCR4 signaling.

SUMMARY OF THE INVENTION

The research of the invention finds that by clearly analyzing the N-terminal protein sequence of CCR4 and resolving the N-terminal protein structure of CCR4 through a two-step model, the N-terminal recombinant protein of CCR4 and its derived triplet (N-CCR4)$_3$ can be effectively synthesized, and the experiment proves that the N-terminal recombinant protein of CCR4 and its derived triplet can bind to the chemokine CCL22 and significantly inhibit the chemotaxis of Treg.

The N-terminal recombinant protein of the chemokine receptor CCR4 provided by the present invention, derivative compound thereof, recombinant protein antibodies and other derivatives or compositions alone or in combination with other compounds or compositions having related uses, has a good clinical application prospect in treating, preventing, inhibiting or ameliorating cancers and diseases or conditions associated with CCR4 signaling.

In one aspect, the invention provides a use of N-terminal recombinant proteins of CCR4, derivative compounds thereof, recombinant protein antibodies and other derivatives or compositions alone or in combination with other compounds or compositions having related uses, for treating, preventing, inhibiting or ameliorating cancers and diseases or conditions associated with CCR4 signaling.

In another aspect, the invention provides N-terminal recombinant proteins of CCR4, derivative compounds thereof, recombinant protein antibodies and other derivatives or compositions, including but not limited to N-terminal recombinant protein of CCR4 (N-CCR4), derivative compounds thereof such as (N-CCR4)$_n$, for example a concatemer (eg. bigeminy or triplet) of N-terminal recombinant proteins, recombinant protein antibodies thereof (N-CCR4)$_n$-Fc, or other structural analogs and the like.

wherein the sequence of N-CCR4 protein is:

(SEQ ID NO. 1)
MNPTDIADTTLDESIYSNYYLYESIPKPCTKEGIKAFGELFLPPLYS wherein the sequence of (N-CCR4)₃ protein is:

(SEQ ID NO. 2)
MNPTDIADTTLDESIYSNYYLYESIPKPCTKEGIKAFGELFLPPLYS

GGGGSGGGGSMNPTDIADTTLDESIYSNYYLYESIPKPCTKEGIKAF

GELFLPPLYSGGGGSGGGGSMNPTDIADTTLDESIYSNYYLYESIPK

PCTKEGIKAFGELFLPPLYSLDPNSSSVDKLAAALEHHHHHH wherein the sequence of (N-CCR4)₃-Fc protein is:

(SEQ ID NO. 3)
MNPTDIADTTLDESIYSNYYLYESIPKPCTKEGIKAFGELFLPPLYS

GGGGSGGGGSMNPTDIADTTLDESIYSNYYLYESIPKPCTKEGIKAF

GELFLPPLYSGGGGSGGGGSMNPTDIADTTLDESIYSNYYLYESIPK

PCTKEGIKAFGELFLPPLYSKLDKTHTCPPCPAPELLGGPSVFLFPP

KPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKA

KGQPREPQVYTLPPSRDELTKNQVSLTCLVKGFYPSDIAVEWESNGQ

PENNYKTTPPVLDSDGSFFLYSKLTVDKSRWQQGNVFSCSVMHEGLH

NHYTQKSLSLSPGK

In another aspect, the N-terminal recombinant protein of CCR4, derivative compounds thereof, recombinant protein antibodies and other derivatives or compositions, can be used alone or in combination with other compounds or compositions having related uses.

In another aspect, the N-terminal recombinant protein of CCR4, derivative compounds thereof, recombinant protein antibodies and other derivatives or compositions, can be administered by oral, parenteral such as intramuscular, intravenous, subcutaneous injection or implantation, inhalation, or topical administration routes, etc., and can be formulated alone or together to form a suitable dosage unit formulation containing conventional non-toxic pharmaceutically acceptable carriers, adjuvants and carriers suitable for each route of administration.

In another aspect, other compounds or compositions for use in combination can be administered by their usual routes and amounts, either simultaneously or sequentially or separately with the compounds or compositions of the present invention. Therapeutic agents that can be administered simultaneously or sequentially or separately with a compound or composition of the present invention include, but are not limited to, conventional drugs for the treatment of inflammatory diseases such as anti-inflammatory drugs, hormone drugs, immunosuppressants, antihistamines, etc., conventional drugs for the treatment of cancers such as chemoradiotherapy drugs, conventional first-line drugs (e.g., cisplatin, vincristine, sorafenib, etc.), immune checkpoint inhibitors (PD-1/PD-L1, CTLA-4, 4-1BB, CD40/CD40L, etc.), and other tumor immune targeting drugs (VEGF/VEGFR, EGF, etc.).

In another aspect, the compounds of the invention can be used in treating, preventing, inhibiting or ameliorating cancers and diseases or conditions associated with CCR4 signaling.

In another aspect, the treatment includes, but is not limited to, 1) allergic disease, such as systemic allergic reaction or hypersensitivity reaction, etc.; 2) inflammatory enteritis, such as Crohn's disease, ulcerative colitis, ileitis and enteritis, etc.; 3) psoriasis and inflammatory skin disease, such as dermatitis, eczema, atopic dermatitis, allergic contact dermatitis, dermatomyositis and urticaria, etc.; 5) vasculitis; 6) spondyloarthropathy; 7) scleroderma; 8) asthma and respiratory allergic disease, such as allergic asthma, exercise-induced asthma, allergic rhinitis, hypersensitivity lung disease; 9) autoimmune disease, such as arthritis, multiple sclerosis, systemic lupus erythematosus, diabetes, nephritis, etc.; 10) graft rejection, such as allograft rejection and graft-versus-host disease, etc.; 11) leukemia, lymphoma, and other blood-borne cancers such as cutaneous T-cell lymphoma, acute lymphocytic leukemia, etc.; 12) other diseases requiring inhibition of undesirable inflammation, such as atherosclerosis, myositis, neurodegenerative disease, encephalitis, meningitis, hepatitis, nephritis, etc.; 13) cancer, including solids tumor and metastatic disease, such as gastric cancer, liver cancer, renal cancer, intestinal cancer, pancreatic cancer, lung cancer, bladder cancer, breast cancer, ovarian cancer, cervical cancer, melanoma, thyroid cancer, prostate cancer, nervous system tumor, etc.

In another aspect, the compounds of the invention and other therapeutic agents that can be used in combination may be administered simultaneously or sequentially or separately for treating, preventing, inhibiting or ameliorating cancers and diseases or conditions associated with CCR4 signaling.

In another aspect, the present invention provides a pharmaceutical composition, which can be formulated as an injection, a tablet or a capsule.

More specifically, the present invention provides the following:

1. A recombinant protein or a derivative thereof, wherein the recombinant protein has an amino acid sequence of the N-terminal portion of CC chemokine receptor 4 (CCR4).

2. The recombinant protein or a derivative thereof of item 1, wherein the amino acid sequence of the recombinant protein is represented by SEQ ID NO. 1.

3. The recombinant protein or a derivative thereof of item 1, wherein the derivative is a concatemer of the recombinant protein or a fusion protein of the recombinant protein with the Fc fragment of an immunoglobulin.

4. The recombinant protein or a derivative thereof of item 1, wherein the derivative is a triplet of the recombinant protein, and the amino acid sequence of the derivative is represented by SEQ ID NO. 2.

5. The recombinant protein or a derivative thereof of item 1, wherein the derivative is a fusion protein of the recombinant protein with the Fc fragment of an immunoglobulin, and the amino acid sequence of the derivative is represented by SEQ ID NO. 3.

6. A pharmaceutical composition comprising the recombinant protein or a derivative thereof of any one of items 1-5.

7. Use of the recombinant protein or a derivative thereof of any one of items 1-5 or the pharmaceutical composition of item 6 in preparation of a medicament for inhibiting the binding of CCR4 to a ligand of CCR 4.

8. Use of the recombinant protein or a derivative thereof of any one of items 1-5 or the pharmaceutical composition of item 6 in preparation of a medicament for treating or preventing a disease or condition associated with CCR4 signaling.

9. The use of item 8, wherein the diseases or condition associated with CCR4 signaling include 1) allergic disease, such as systemic allergic reaction or hypersensitivity reaction; 2) inflammatory enteritis, such as Crohn's disease, ulcerative colitis, ileitis and enteritis; 3) psoriasis and inflammatory skin disease, such as dermatitis, eczema, atopic dermatitis, allergic contact dermatitis, dermatomyositis and urticaria; 5) vasculitis; 6) spondyloarthropathy; 7) scleroderma; 8) asthma and respiratory allergic disease, such as allergic asthma, exercise-induced asthma, allergic rhinitis, hypersensitivity lung disease; 9) autoimmune disease, such as arthritis, multiple sclerosis, systemic lupus erythematosus, diabetes, nephritis; 10) graft rejection, such as allograft rejection and graft-versus-host disease; 11) leukemia, lymphoma, and other blood-borne cancers such as cutaneous T-cell lymphoma, acute lymphocytic leukemia; 12) other diseases requiring inhibition of undesirable inflammation, such as atherosclerosis, myositis, neurodegenerative disease, encephalitis, meningitis, hepatitis, nephritis; 13) cancer, including solids tumor and metastatic tumor, such as gastric cancer, liver cancer, renal cancer, intestinal cancer, pancreatic cancer, lung cancer, bladder cancer, breast cancer, ovarian cancer, cervical cancer, melanoma, thyroid cancer, prostate cancer, nervous system tumor.

10. The use of item 8, wherein the disease or condition associated with CCR4 signaling is a cancer.

11. Use of the recombinant protein or a derivative thereof of any one of items 1-5 or the pharmaceutical composition of item 6 for inhibiting the binding of CCR4 to a ligand of CCR 4.

12. Use of the recombinant protein or a derivative thereof of any one of items 1-5 or the pharmaceutical composition of item 6 for treating or preventing a disease or condition associated with CCR4 signaling.

SPECIFIC MODE FOR CARRY OUT THE INVENTION

Example 1: Prediction of N-Terminal Protein N-CCR4 of CCR4

Figure 1A:
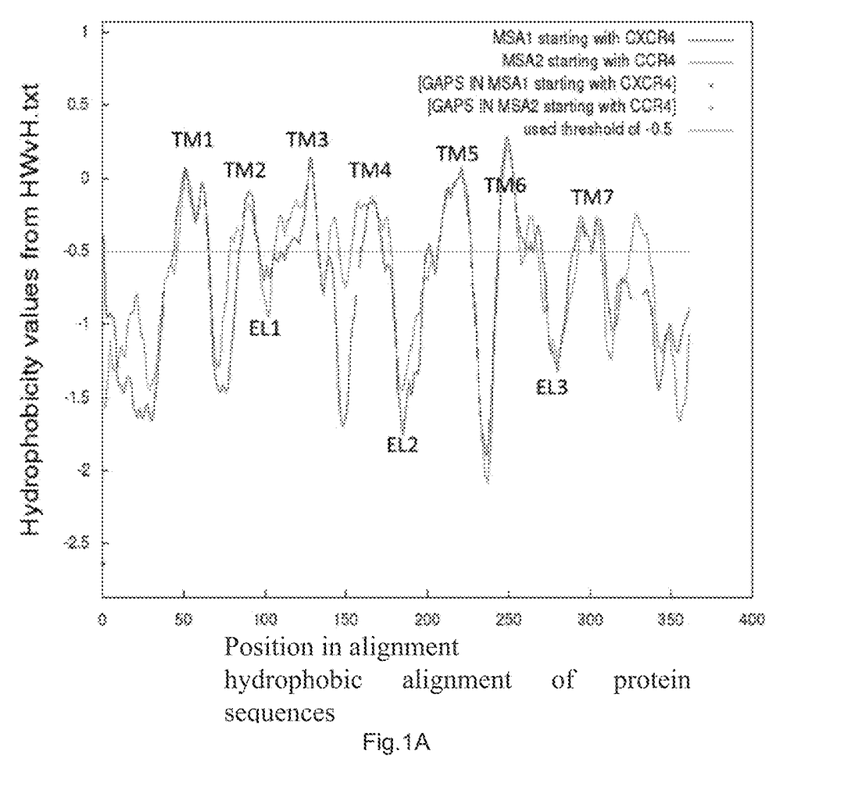
FIG. 1A shows a hydropathy plot and prediction of the N-terminal region of N-CCR4 of CCR4.
Figure 1B:
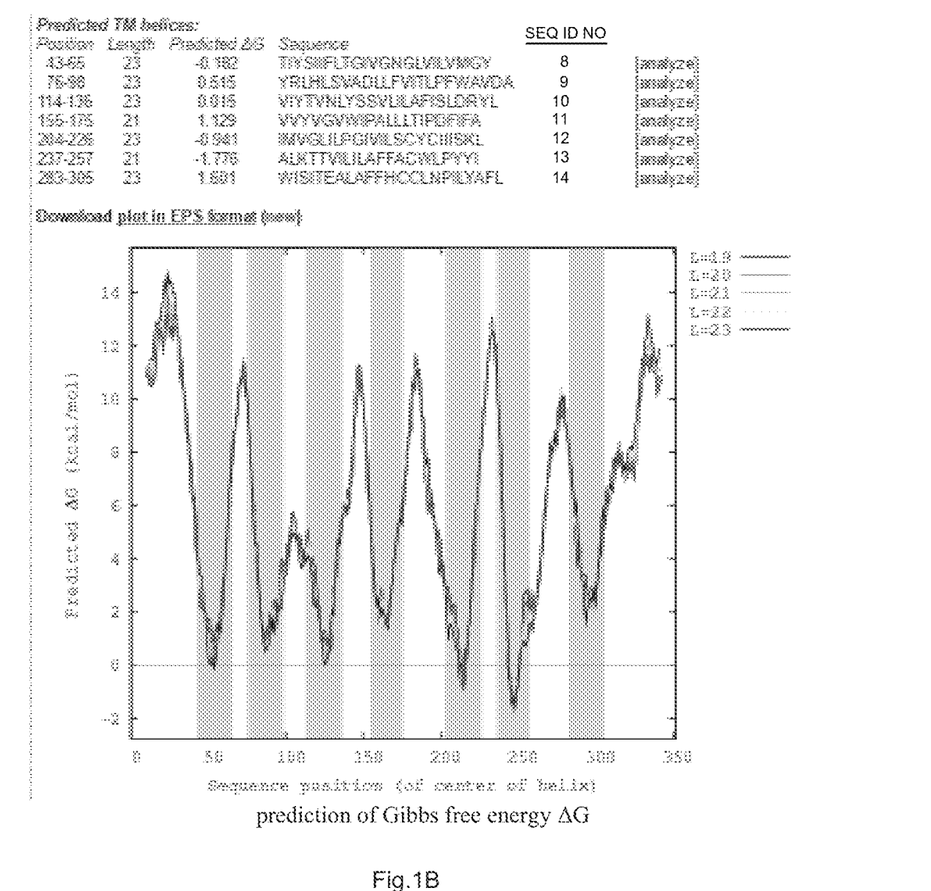
FIG. 1B shows predicted transmembrane helices and predicted Gibbs free energy.

1. The N-terminal protein N-CCR4 of CCR4 was predicted by hydrophobic alignment of CCR4 to CXCR4 protein sequence (located on the World-Wide Web at bioinfo.mpg.de/AlignMe/AlignMe_MSA.html) and by calculation of Gibbs free energy ΔG of CCR4 protein sequence (ΔG predictor sever v1.0, located on the internet at: dgpred.cbr.su.se) (FIG. 1A, B).

The sequence of N-CCR4 protein is:

(SEQ ID NO. 1)
MNPTDIADTTLDESIYSNYYLYESIPKPCTKEGIKAFGELFLPPLYS

2. Purification of N-CCR4 Derived Protein (N-CCR4)$_3$

Figure 1C:
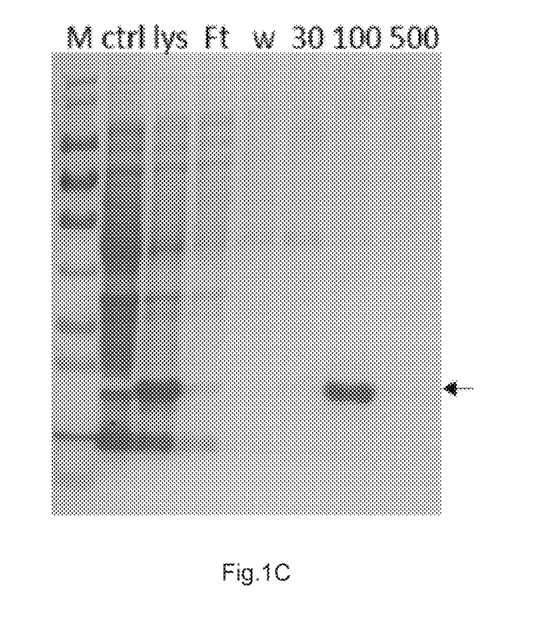
FIG. 1C and FIG. 1D show the purification of its derived proteins (N-CCR4)$_3$, (N-CCR4)$_3$-Fc.

The codon-optimized sequence of (N-CCR4)$_3$ DNA was cloned into pET22b(+) vector (Novagen, Cat. number 69744-3) via NdeI and BamHI cleavage sites, and transformed into Transetta competent cells (TransGen, Cat. number CD801-01). The culture broth shaken overnight was inoculated into a new LB medium at a ratio of 1:100, and when the OD600 of the culture broth was 0.6, IPTG (amresco, cat: 0487-1G) with a final concentration of 1 mM was added, and the protein expression was induced at 25° C., 220 rpm/min for 10 hours. After resuspending the cells in PBS, the cells were disrupted by a high pressure cell homogenizer (JN-02C low-temperature ultrahigh-pressure continuous flow cell homogenizer), loaded on a nickel column (BBI, cat #C600793) and eluted with Tris-HCl (pH8.0) buffer containing 100 mM imidazole, and then dialyzed twice against 2 L PBS. A pre-induced control sample(ctrl), a post-induced lysis sample(lys), a flow through sample(Ft), a washing sample (w), a 30 mM imidazole-elution sample, a 100 mM imidazole-elution sample, and a 500 mM imidazole-elution sample are detected by 12% SDS-PAGE (FIG. 1C).

The codon optimized sequence of (N-CCR4)$_3$ protein DNA is:

(SEQ ID NO. 4)
ATGAATCCGACCGATATTGCAGATACCACACTGGATGAAAGCATCTAT

AGCAACTATTATCTGTATGAGAGCATTCCGAAACCGTGTACCAAAGAA

GGTATTAAAGCATTTGGCGAACTGTTTCTGCCTCCGCTGTATAGCGGT

GGTGGTGGTAGTGGTGGCGGTGGTTCAATGAACCCGACAGATATCGCC

GACACAACCCTGGATGAATCAATTTATTCCAACTACTACCTGTACGAG

TCAATCCCGAAACCTTGCACAAAAGAGGGCATCAAAGCCTTTGGTGAG

CTGTTTTTACCGCCTCTGTATTCAGGCGGTGGCGGTAGCGGAGGTGGC

GGAAGCATGAATCCTACAGACATTGCGGATACGACCCTGGACGAGAGC

ATTTATTCAAATTACTATTTATACGAAAGCATCCCGAAGCCATGTACG

AAAGAGGGAATTAAGGCGTTCGGTGAATTATTTCTGCCACCGTTATAT

AGCTTGGATCCGAATTCGAGCTCCGTCGACAAGCTTGCGGCCGCACTC

GAGCACCACCACCACCACCAC

The sequence of (N-CCR4)$_3$ protein is:

(SEQ ID NO. 2)
MNPTDIADTTLDESIYSNYYLYESIPKPCTKEGIKAFGELFLPPLYSG

GGGSGGGGSMNPTDIADTTLDESIYSNYYLYESIPKPCTKEGIKAFGE

LFLPPLYSGGGGSGGGGSMNPTDIADTTLDESIYSNYYLYESIPKPCT

KEGIKAFGELFLPPLYSLDPNSSSVDKLAAALEHHHHHH

3. Purification of N-CCR4-Derived Antibody (N-CCR4)$_3$-Fc

Figure 1D:
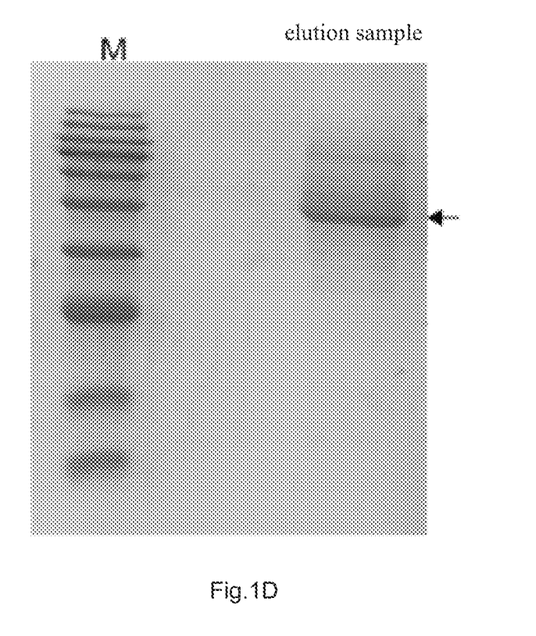

The murine kappa III signal peptide-(N-CCR4)$_3$-Fc DNA sequence was cloned into the pCEP4 vector by KpnI and BamHI, wherein the murine kappa III signal peptide is a secretory signal peptide and Fc is a human IgG1 Fc. The constructed plasmid was transfected into 293FT cells using PEI (Shanghai Qifa Biological Reagent Co. Ltd., cat #24765-2), and the supernatant was collected on the third day after transfection and then purified with protein A prepacked gravity column (BBI, cat #C600951). The elution samples were taken and detected on a 10% SDS-PAGE (FIG. 1D).

The sequence of (N-CCR4)₃-Fc DNA:

(SEQ ID NO. 5)
ATGGAGACAGACACACTCCTGCTATGGGTACTGCTGCTCTGGGTTCCA

GGTTCCACTGGTGACTCGATGAACCCCACCGACATCGCCGACACCACC

CTCGACGAGAGCATCTACAGCAACTACTACCTGTACGAAAGCATCCCC

AAACCCTGCACCAAAGAAGGCATCAAAGCCTTCGGCGAGCTGTTCCTC

CCCCCCCTGTACAGCGGCGGCGGTGGATCTGGCGGCGGAGGATCAATG

AACCCCACAGACATCGCCGATACCACCCTGGACGAAAGCATTTACAGC

AATTACTACCTGTATGAGTCCATCCCCAAACCTTGCACCAAAGAGGGC

ATCAAGGCCTTCGGCGAACTGTTCCTCCCACCCCTGTACAGTGGCGGC

GGCGGAAGCGGAGGCGGAGGAAGCATGAACCCCACTGACATCGCCGAC

ACAACCCTCGACGAAAGCATATACAGCAATTATTACCTGTACGAGTCC

ATCCCTAAACCCTGCACAAAGGAAGGCATCAAGGCATTCGGAGAGCTG

TTCCTGCCCCCCCTGTATAGCAAGCTTGACAAAACTCACACATGCCCA

CCGTGCCCAGCACCTGAACTCCTGGGGGGACCGTCAGTCTTCCTCTTC

CCCCCAAAACCCAAGGACACCCTCATGATCTCCCGGACCCCTGAGGTC

ACATGCGTGGTGGTGGACGTGAGCCACGAAGACCCTGAGGTCAAGTTC

AACTGGTACGTGGACGGCGTGGAGGTGCATAATGCCAAGACAAAGCCG

CGGGAGGAGCAGTACAACAGCACGTACCGTGTGGTCAGCGTCCTCACC

GTCCTGCACCAGGACTGGCTGAATGGCAAGGAGTACAAGTGCAAGGTC

TCCAACAAAGCCCTCCCAGCCCCCATCGAGAAAACCATCTCCAAAGCC

AAAGGGCAGCCCCGAGAACCACAGGTGTACACCCTGCCCCCATCCCGG

GATGAGCTGACCAAGAACCAGGTCAGCCTGACCTGCCTGGTCAAAGGC

TTCTATCCCAGCGACATCGCCGTGGAGTGGGAGAGCAATGGGCAGCCG

GAGAACAACTACAAGACCACGCCTCCCGTGCTGGACTCCGACGGCTCC

TTCTTCCTCTACAGCAAGCTCACCGTGGACAAGAGCAGGTGGCAGCAG

GGGAACGTCTTCTCATGCTCCGTGATGCATGAGGGTCTGCACAACCAC

TACACGCAGAAGAGCCTCTCCCTGTCTCCGGGTAAATAATAA

The sequence of (N-CCR4)₃-Fc protein:

(SEQ ID NO. 3)
MNPTDIADTTLDESIYSNYYLYESIPKPCTKEGIKAFGELFLPPLYSG

GGGSGGGGSMNPTDIADTTLDESIYSNYYLYESIPKPCTKEGIKAFGE

LFLPPLYSGGGGSGGGGSMNPTDIADTTLDESIYSNYYLYESIPKPCT

KEGIKAFGELFLPPLYSKLDKTHTCPPCPAPELLGGPSVFLFPPKPKD

TLMISRTPEVTCVVVDVSHEDPEVKFNWYVDGVEVHNAKTKPREEQYN

STYRVVSVLTVLHQDWLNGKEYKCKVSNKALPAPIEKTISKAKGQPRE

PQVYTLPPSRDELTKNQVSLTCLVKGFYPSDIAVEWESNGQPENNYKT

TPPVLDSDGSFFLYSKLTVDKSRWQQGNVFSCSVMHEGLHNHYTQKSL

SLSPGK

Example 2: The Experiment of Interaction Between (N-CCR4)₃ and CCL22

The GST-pulldown experiment can verify whether two proteins interact with each other, so that it is verified that (N-CCR4)₃ interacts with CCL22 by GST-pulldown experiment.

1. The Expression of CCL22-GST Protein

The CCL22 DNA sequence was codon optimized and CCL22 and GST were cloned into pET22b vector via the cleavage sites NdeI, BamHI and HindIII. Transetta competent cells were transformed. The culture broth shaken overnight was inoculated into a new LB medium at a ratio of 1:100, and when the OD600 of the culture broth was 0.6, IPTG (amresco, cat: 0487-1G) at a final concentration of 1 mM was added, and the protein expression was induced at 20° C., 210 rpm/min for 10 hours. After resuspending the cells in PBS, the cells were disrupted by a high pressure cell homogenizer, loaded on GST agarose (BBI, cat #C600031) overnight, washed with 150 mM NaCl, 1 mM DTT (amresco, cat #0281-5G) 10 mM Tris-HCl (pH8.0) buffer for 10 column volumes, and then eluted with 10 mM reduced glutathione (BBI, cat #70-18-8) 150 mM NaCl, 1 mM DTT Tris-HCl (pH8.0) buffer, and then dialyzed twice against 2 L PBS.

The sequence of CCL22-GST DNA:

(SEQ ID NO. 6)
ATGGGTCCGTATGGTGCAAATATGGAAGATAGCGTTTGTTGCCGTGAT

TATGTTCGTTATCGTCTGCCGCTGCGTGTTGTTAAACACTTTTATTGG

ACCAGCGATAGCTGTCCGCGTCCGGGTGTTGTTCTGCTGACCTTTCGT

GATAAAGAAATTTGTGCAGATCCGCGTGTTCCGTGGGTTAAAATGATT

CTGAATAAACTGAGCCAGGATCCGGGTGGCCCGGGTATGTCCCCTATA

CTAGGTTATTGGAAAATTAAGGGCCTTGTGCAACCCACTCGACTTCTT

TTGGAATATCTTGAAGAAAAATATGAAGAGCATTTGTATGAGCGCGAT

GAAGGTGATAAATGGCGAAACAAAAAGTTTGAATTGGGTTTGGAGTTT

CCCAATCTTCCTTATTATATTGATGGTGATGTTAAATTAACACAGTCT

ATGGCCATCATACGTTATATAGCTGACAAGCACAACATGTTGGGTGGT

TGTCCAAAAGAGCGTGCAGAGATTTCAATGCTTGAAGGAGCGGTTTTG

GATATTAGATACGGTGTTTCGAGAATTGCATATAGTAAAGACTTTGAA

ACTCTCAAAGTTGATTTTCTTAGCAAGCTACCTGAAATGCTGAAAATG

TTCGAAGATCGTTTATGTCATAAAACATATTTAAATGGTGATCATGTA

ACCCATCCTGACTTCATGTTGTATGACGCTCTTGATGTTGTTTTATAC

ATGGACCCAATGTGCCTGGATGCGTTCCCAAAATTAGTTTGTTTTAAA

AAACGTATTGAAGCTATCCCACAAATTGATAAGTACTTGAAATCCAGC

AAGTATATAGCATGGCCTTTGCAGGGCTGGCAAGCCACGTTTGGTGGT

GGCGACCATCCTCCAAAATGA

The sequence of CCL22-GST protein:

(SEQ ID NO. 7)
MGPYGANMEDSVCCRDYVRYRLPLRVVKHFYWTSDSCPRPGVVLLTFR

DKEICADPRVPWVKMILNKLSQDPGGPGMSPILGYWKIKGLVQPTRLL

-continued

LEYLEEKYEEHLYERDEGDKWRNKKFELGLEFPNLPYYIDGDVKLTQS

MAIIRYIADKHNMLGGCPKERAEISMLEGAVLDIRYGVSRIAYSKDFE

TLKVDFLSKLPEMLKMFEDRLCHKTYLNGDHVTHPDFMLYDALDVVLY

MDPMCLDAFPKLVCFKKRIEAIPQIDKYLKSSKYIAWPLQGWQATFGG

GDHPPK

2. The Expression of GST Protein

Transetta competent cells were transformed with pGEX-6P-1 plasmid (GE, cat #27-4597-01). The culture broth shaken overnight was inoculated into a new LB medium at a ratio of 1:100, and when the OD600 of the culture broth was 0.6, IPTG (amresco, cat: 0487-1G) at a final concentration of 1 mM was added, and the protein expression was induced at 25° C., 210 rpm/min for 10 hours. After resuspending the cells in PBS, the cells were disrupted by a high pressure cell homogenizer, loaded on GST agarose (BBI, cat #C600031) overnight, and washed with 10 mM Tris-HCl, 150 mM NaCl, 1 mM DTT (amresco, cat #0281-5G) buffer for 10 column volumes, and then eluted with 10 mM reduced glutathione (BBI, cat #70-18-8) 150 mM NaCl, 1 mM DTT Tris-HCl (pH8.0) buffer, and then dialyzed twice against 2 L PBS.

Figure 2:
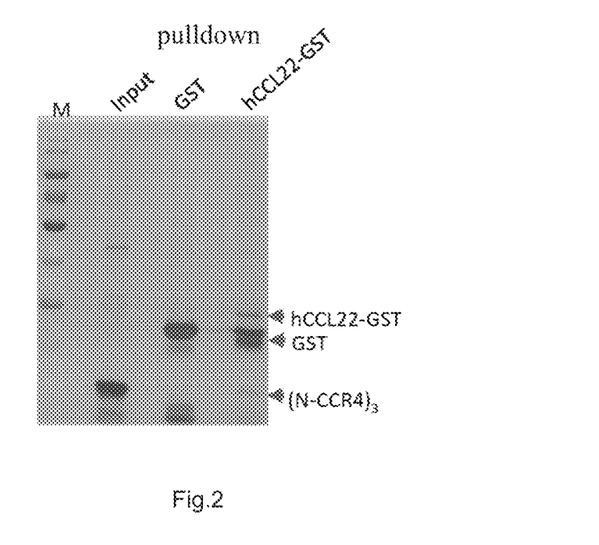
FIG. 2 shows the experiment of interaction between (N-CCR4)$_3$ and CCL22.

3. GST Pulldown 120 ng CCL22-GST and GST protein were mixed with 360 ng (N-CCR4)$_3$ respectively; 20 ul GST agarose was added respectively; and the liquid volume was made up to 600 ul with PBS; and then rotated to bind at 4° C. for 4 h; washed with PBS+0.1% Triton-100 for 3 times, then washed with PBS for 3 times; the proteins on the beads were dissolved with 30 ul of 1× loading buffer, boiled for 3 minutes, centrifuged at high speed; 1 ul of supernatant was taken to 12% SDS PAGE gel and silver stained (Biyunyan, Rapid silver staining kit, cat #P0017S) for detection. As shown in FIG. 2, (N-CCR4)$_3$ interacted with CCL22.

Example 3: Experiment Showing that (N-CCR4)$_3$ Inhibits the Chemotaxis of Treg Cell Chemotaxis experiment is a common model for observing the chemotactic migration of cells and therefore is used to verify the inhibitory effect of (N-CCR4)$_3$ on the chemotaxis of Treg cell.

Figure 3:
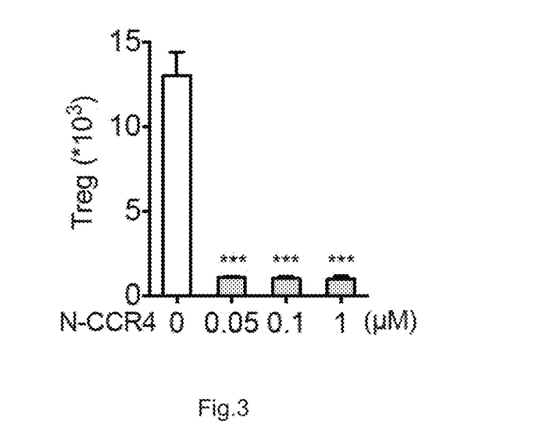
FIG. 3 shows an experiment in which (N-CCR4)$_3$ inhibits the chemotaxis of Treg cells.

Naïve CD4+ T lymphocytes were sorted and stimulated with anti-CD3 (2 μg/mL), anti-CD28 (1 μg/mL), TGF β (1 ng/mL) and IL-2 (4 ng/mL) for 2 days; the induced Treg cells were harvested and placed in the upper chamber of the chemotactic chamber by 2×10$^5$/well; the tumor cell culture supernatant and 0.05 μM, 0.1 μM and 1 μM (N-CCR4)$_3$ recombinant protein were added respectively to the lower chamber; after 4 hours, Treg cells in the lower chamber were harvested and counted for statistical analysis, as shown in FIG. 3, the chemotactic movement of Treg cells was significantly inhibited by adding (N-CCR4)$_3$.

The invention claimed is:

1. A isolated recombinant protein or a derivative thereof, wherein the recombinant protein consists of the amino acid sequence of the N-terminal portion of CC chemokine receptor 4 (N-CCR4), as shown in SEQ ID NO: 1, wherein the derivative is a concatemer of the recombinant protein as shown by (N-CCR4)$_n$, wherein n is 2 or 3, or a fusion protein of the recombinant protein with an Fc fragment of an immunoglobulin as shown by (N-CCR4)$_m$-Fc, wherein m is 1, 2 or 3.

2. The isolated recombinant protein or a derivative thereof of claim 1, wherein the amino acid sequence of the derivative is shown in SEQ ID NO. 2.

3. The isolated recombinant protein or a derivative thereof of claim 1, wherein the amino acid sequence of the derivative is shown in SEQ ID NO: 3.

4. A pharmaceutical composition comprising the recombinant protein or a derivative thereof of claim 1.

5. A method of treating a subject having a disease or condition associated with CCR4 signaling, the method comprising administering to the subject the isolated recombinant protein or a derivative according to claim 1 or a pharmaceutical composition comprising the isolated recombinant protein or a derivative thereof of claim 1.

6. The method of claim 5, wherein the disease or condition associated with CCR4 signaling is selected from the group consisting of: an allergic disease, inflammatory enteritis, psoriasis, an inflammatory skin disease, vasculitis, spondyloarthropathy, scleroderma, asthma, a respiratory allergic disease, an autoimmune disease, graft rejection, leukemia, lymphoma, a blood-borne cancer, a disease requiring inhibition of undesirable inflammation, and a cancer.

7. The method of claim 5, wherein the disease or condition associated with CCR4 signaling is a cancer.

8. The method of claim 6, wherein the allergic disease is systemic allergic reaction or hypersensitivity reaction.

9. The method of claim 6, wherein the inflammatory enteritis is selected from the group consisting of Crohn's disease, ulcerative colitis, ileitis and enteritis.

10. The method of claim 6, wherein the inflammatory skin disease is selected from the group consisting of dermatitis, eczema, atopic dermatitis, allergic contact dermatitis, dermatomyositis and urticaria.

11. The method of claim 6, wherein the respiratory allergic disease is selected from the group consisting of allergic asthma, exercise-induced asthma, allergic rhinitis and hypersensitivity lung disease.

12. The method of claim 6, wherein the autoimmune disease is selected from the group consisting of arthritis, multiple sclerosis, systemic lupus erythematosus, diabetes, and nephritis.

13. The method of claim 6, wherein the graft rejection is selected from the group consisting of allograft rejection and graft-versus-host disease.

14. The method of claim 6, wherein the blood-borne cancer is selected from the group consisting of cutaneous T-cell lymphoma and acute lymphocytic leukemia.

15. The method of claim 6, wherein the disease requiring inhibition of undesirable inflammation is selected from the group consisting of atherosclerosis, myositis, neurodegenerative disease, encephalitis, meningitis, hepatitis and nephritis.

16. The method of claim 6, wherein the cancer is selected from the group consisting of a solid tumor, a metastatic tumor, a liver cancer, a renal cancer, an intestinal cancer, a pancreatic cancer, a lung cancer, a bladder cancer, a breast cancer, an ovarian cancer, a cervical cancer, a melanoma, a thyroid cancer, a prostate cancer and a nervous system tumor.

17. The method of claim 16, wherein the metastatic tumor is a gastric cancer.

18. An isolated recombinant protein comprising:
a concatemer of the amino acid sequence of the N-terminal portion of CC chemokine receptor 4 (N-CCR4), as shown in SEQ ID NO: 1, wherein the concatemer has a structure of (N-CCR4)$_n$, wherein n is 2 or 3, or
a fusion protein of the N-terminal portion of CC chemokine receptor 4 (N-CCR4), as shown in SEQ ID NO: 1, with an Fc fragment of an immunoglobulin as shown by (N-CCR4)$_m$-Fc, wherein m is 1, 2 or 3.

* * * * *

UNITED STATES PATENT AND TRADEMARK OFFICE
CERTIFICATE OF CORRECTION

PATENT NO. : 11,254,730 B2
APPLICATION NO. : 16/758825
DATED : February 22, 2022
INVENTOR(S) : Pengyuan Yang It is certified that error appears in the above-identified patent and that said Letters Patent is hereby corrected as shown below:

In the Specification

Column 2, Line 19, delete "T cell" and insert --T-cell--.

Column 5, Line 60, delete "sever" and insert --server--.

Column 5, Line 61, delete "(FIG." and insert --(FIGS.--.

Column 6, Line 4, delete "Ndel" and insert --NdeI--.

Column 8, Line 11, delete "Ndel," and insert --NdeI,--.

Column 10, Line 7, delete "Biyunyan" and insert --Beyotime--.

Column 10, Line 18, delete "CD4+" and insert --$CD4^+$--.

Column 10, Line 19, delete "TGF β" and insert --TGF-β--.

Signed and Sealed this
Twenty-first Day of June, 2022

Katherine Kelly Vidal
*Director of the United States Patent and Trademark Office*